United States Patent [19]

Barnett et al.

[11] Patent Number: 4,544,566

[45] Date of Patent: Oct. 1, 1985

[54] 3-HYDROXY-4-ALKYLOXYPHENYL HETEROCYCLIC CARBONATES

[75] Inventors: Ronald E. Barnett, Suffern; Jed A. Riemer, Scarsdale; Paul R. Zanno, Nanuet, all of N.Y.

[73] Assignee: General Foods Corporation, White Plains, N.Y.

[21] Appl. No.: 594,459

[22] Filed: Mar. 29, 1984

[51] Int. Cl.[4] .................. A23L 1/236; C07C 69/96
[52] U.S. Cl. ............................ 426/548; 260/463
[58] Field of Search ................... 426/548; 260/463

[56] References Cited

U.S. PATENT DOCUMENTS

| | | | |
|---|---|---|---|
| 4,182,726 | 1/1980 | Illuminati et al. | 260/463 |
| 4,209,431 | 6/1980 | Clark et al. | 260/463 |
| 4,348,333 | 9/1982 | DuBois | 426/548 |

FOREIGN PATENT DOCUMENTS 0091218  8/1976  Japan .................. 426/548

*Primary Examiner*—Raymond Jones
*Assistant Examiner*—Elizabeth C. Weimar
*Attorney, Agent, or Firm*—Joseph T. Harcarik; Linn I. Grim; Daniel J. Donovan

[57] ABSTRACT

Novel 3-hydroxy-4-alkyloxyphenyl heterocyclic carbonates suited as sweeteners in foodstuff, said carbonates having the following basic structure:

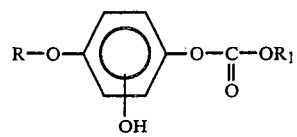

10 Claims, No Drawings

3-HYDROXY-4-ALKYLOXYPHENYL HETEROCYCLIC CARBONATES

BACKGROUND OF THE INVENTION

1. Field of the Invention

This invention relates to a novel group of compounds and more particular to a novel group of compounds particularly well suited as sweeteners in edible foodstuff.

2. Description of the Prior Art

Sweetness is one of the primary taste cravings of both animals and humans. Thus, the utilization of sweetening agents in foods in order to satisfy this sensory desire is well established.

Naturally occurring carbohydrate sweeteners such as sucrose, are still the most widely used sweetening agents. While these naturally occurring carbohydrates, i.e., sugars, generally fulfill the requirements of sweet taste, the abundant usage thereof does not occur without deleterious consequence, e.g., high caloric intake and nutritional imbalance. In fact, oftentimes the level of these sweeteners required in foodstuffs is far greater than the level of the sweetener that is desired for economic, dietic or other functional consideration.

In an attempt to eliminate the disadvantages concomitant with natural sweeteners, considerable reasearch and expense have been devoted to the production of artificial sweeteners, such as for example, saccharin, cyclamate, dihydrochalcone, aspartame, etc. While some of these artificial sweeteners satisfy the requirements of sweet taste without caloric input, and have met with considerable commercial success, they are not, however, without their own inherit disadvantages. For example, many of these artificial sweeteners have the disadvantages of high cost, as well as delay in the perception of the sweet taste, persistent lingering of the sweet taste, and a very objectionable bitter, metallic aftertaste when used in food products.

Since it is believed that many disadvantages of artificial sweeteners, particularly aftertaste, is a function of the concentration of the sweetener, it has been previously suggested that these effects could be reduced or eliminated by combining artificial sweeteners such as saccharin, with other ingredients or natural sugars, such as sorbitol, dextrose, maltose etc. These combined products, however, have not been entirely satisfactory either. Some U.S. patents which disclose sweetener mixtures include for example, U.S. Pat. No. 4,228,198; U.S. Pat. No. 4,158,068; U.S. Pat. No. 4,154,862; U.S. Pat. No. 3,717,477.

Also much work has continued in an attempt to develop and identify compounds that have a sweet taste. For example, in Yamato, et al., Chemical Structure and Sweet Taste Of Isocoumarin and Related Compounds, Chemical Pharmaceutical Bulletin, Vol. 23, p. 3101–3105 (1975) and in Yamato et al. Chemical Structure and Sweet Taste Of Isocoumarins and Related Compound, Chemical Senses And Flavor, Vol. 4 No. 1, p. 35–47 (1979) a variety of sweet structures are described. For example, 3-Hydroxy-4-methoxybenzyl phenyl ether is described as having a faint sweet taste.

Despite the past efforts in this area, research continues. Accordingly, it is desired to find a compound that provides a sweet taste when added to foodstuff or one which can reduce the level of sweetener normally employed and thus eliminate or greatly diminish a number of disadvantages associated with prior art sweeteners.

SUMMARY OF THE INVENTION

This invention pertains to sweetness compounds of the structure:

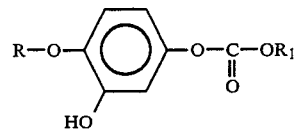

wherein:
R is methyl or ethyl;
$R_1$ is of the formula:

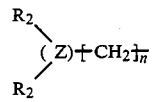

wherein Z is a five-membered heterocyclic ring in which the hetero atom is at least one of S, O, N and $NR_2$; wherein n is an integer from 0 to 1 when Z is a fully-saturated heterocyclic ring and, otherwise n=1, each $R_2$ is selected from the group consisting of H, $CH_3$, $CH_2CH_3$, $CH_2CH_2CH_3$, $CH(CH_3)_2$, OH, $OCH_3$, $CH(OH)CH_3$, $OCH_2CH_3$, $OCH(CH_3)_2$, $CH_2OH$, $CH_2CH_2OH$, $CH_2CHOHCH_3$, $CH_2OCH_3$, CHO, $COCH_3$, $COCH_2CH_3$, $CH_2COCH_3$, and $COOCH_3$ with the proviso that $R_1$ contain no more than 12 carbon atoms; and salts thereof.

The heterocyclic rings representative of Z include both saturated and unsaturated rings, e.g., furyl, tetrahydrothienyl, pyrrl, thiazolyl, imidazolyl, oxazolyl, and the like. For convenience, the unsaturated heterocyclics are referred to in the specification and claims as the "aromatic heterocyclic rings".

Most of the compounds of the formula described hereinabove are sweeteners, the sweetness of which is many times that of comparable amounts of sucrose. The sweetness of compounds of the formula can be readily determined by a simple test procedure described herein.

Several compounds of the formula when tested for sweetness showed little, if any, sweetness to sucrose, whereas most compounds have greater sweetness than sucrose, e.g., 100–300 time greater. In general, the sweetener compound should possess a sweetness at least five times greater, preferably 30 times greater and more preferably 100 times greater than sucrose on comparable weight basis.

These compound in addition to having a sweet taste, function as a low calorie sweetening agent when employed with a foodstuff.

DESCRIPTION OF THE PREFERRED EMBODIMENTS

In accordance with the present invention, the preferred novel compounds are of the formula:

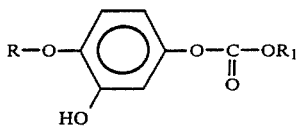

wherein:

R is selected rom the group consisting of methyl and ethyl;

R$_1$ is of the formula

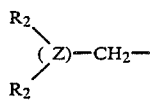

wherein Z is a five membered aromatic heterocyclic ring in which the hetero atom is at least one of S, O, 9 and CR$_2$; and R$_2$ is selected from the group consisting of H, CH$_3$, CH$_2$CH$_3$, CH$_2$CH$_2$CH$_3$, CH(CH$_3$)$_2$, OH, CCH$_3$, OCH$_2$CH$_3$, CH(OH)CH$_3$, OCH(CH$_3$)$_2$, CH$_2$OH, CH$_2$CHOHCH$_3$, CH$_2$OCH$_3$, CHO, COCH$_3$, COCH$_2$CH$_3$, CH$_2$COCH$_3$, and COOCH$_3$ with the proviso that R$_1$ contain no more than 12 carbon atoms; and salts thereof.

Preferably R$_1$ will contain no more than 10 carbon atoms and more preferably will contain no more than 8 carbon atoms.

Illustrative compounds within the scope of the present invention include:

3-hydroxy-4-ethoxyphenyl 2-furfuryl carbonate
3-hydroxy-4-methoxyphenyl 3-tetrahydrofurfuryl carbonate
3-hydroxy-4-methoxyphenyl 2-thienylmethyl carbonate
3-hydroxy-4-methoxyphenyl 3-thienylmethyl carbonate
3-hydroxy-4-methoxyphenyl 3-furfuryl carbonate
3-hydroxy-4-methoxyphenyl 5-methyl-2-furfuryl carbonate
3-hydroxy-4-methoxyphenyl 5-methyl-2-thienylmethyl carbonate
3-hydroxy-4-methoxyphenyl 5-isopropyl-2-thienylmethyl carbonate
3-hydroxy-4-methoxyphenyl 2-tetrahydrothienylmethyl carbonate
3-hydroxy-4-methoxyphenyl N-acetyl-2-pyrrylmethyl carbonate
3-hydroxy-4-methoxyphenyl 5-acetyl-2-thienylmethyl carbonate
3-hydroxy-4-methoxyphenyl 5-methoxy-2-thienylmethyl carbonate
3-hydroxy-4-methoxyphenyl 3,5-dimethyl-2-thienylmethyl carbonate
3-hydroxy-4-methoxyphenyl 2-thiazolylmethyl carbonate
3-hydroxy-4-methoxyphenyl 5-thiazolylmethyl carbonate
3-hydroxy-4-methoxyphenyl 2-oxazolylmethyl carbonate
3-hydroxy-4-methoxyphenyl 2-imidazolylmethyl carbonate
3-hydroxy-4-methoxyphenyl 2-tetrahydrofurfuryl carbonate
3-hydroxy-4-methoxyphenyl 2-pyrrylmethyl carbonate Of these, the preferred are those in which the heterocyclic ring is an aromatic heterocyclic ring, e.g., furan, thiophene, thiazole, pyrrole and oxazole.

These novel compounds are effective sweetness agents when used alone or in combination with other sweeteners in foodstuffs. For example, other natural and/or artificial sweeteners which may be used with the novel compounds of the present invention include sucrose, fructose,, corn syrup solids, dextrose, xylitol, sorbitol, mannitol, acetosulfam, thaumatin, invert sugar, saccharin, cyclamate, dihydrochalcone, hydrogenated glucose syrups, aspartame (L-aspartyl-L-phenylalanine methyl ester) and other dipeptides, glycyrrhizin and stevioside and the like.

Typical foodstuffs, including pharmaceutical preparations, in which the sweetness agents of the present invention may be used are, for example, beverages including soft drinks, carbonated beverages, ready to mix beverages and the like, infused foods (e.g., vegetables or fruits), sauces, condiments, salad dressings, juices, syrups, desserts, including puddings, gelatin and frozen desserts, like ice creams, sherbets and icings, confections, toothpaste, mouthwash, chewing gum, cereals, baked goods, intermediate moisture foods (e.g. dog food) and the like.

In order to achieve the effects of the present invention, the compounds described herein are generally added to the food product at a level which is effective to perceive sweetness in the food stuff and suitably is in an amount in the range of from about 0.0001 to 2% by weight based on the consumed product. Greater amounts are operable but not practical. Preferred amounts are in the range of from about 0.0005 to about 1% of the foodstuff. Generally, the sweetening effect provided by the present compound is experienced over a wide pH range, e.g. 2 to 10 preferably 3 to 7 and in buffered and unbuffered formulations.

It is preferred then when the compounds are used in the foodstuff that the compounds have a sucrose equivalent of at least 1 percent by weight, more preferrably that they have a sucrose equivalent of at least 5 percent by weight and most preferrably they have a sucrose equivalent of at least 7 percent by weight.

A taste procedure for determination of sweetness merely involves the determination of sucrose equivalency.

The sucrose equivalence of a sweetener is readily determined. For example, the amount of a sweetener that is equivalent to 10 weight percent aqueous sucrose can be determined by having a panel of tasters taste the solution of a sweetener and match its sweetness to the standard solution of sucrose. Obviously, sucrose equivalents for other than 10 weight percent are determined by matching the appropriate sucrose solutions.

It is desired that when the sweetening agent of this invention is employed in combination with another sweetener the sweetness equivalence of the other sweetener is equal to or above about 1 percent sucrose equivalence. Preferably the combination of sweeteners provides a sucrose equivalence in the range of from about 3 weight percent to about 40 weight percent and most preferably 4 weight percent to about 15 weight percent.

In order to prepare the compounds of the present invention an esterification reaction is employed. A 3-benzyloxy-4-R-oxyphenol is esterified with a chloroformate of the R$_1$ moiety (e.g., R$_1$OCOCl). This provides a 3-benzyloxy-4-R-oxyphenyl R$_1$ carbonate. This is subsequently converted to the desired 3-hydroxy-4-R-oxyphenyl $R_1$ carbonate.

For example, when R is methyl then 3-benzyloxy-4-methoxyphenol is used for the esterification reaction. To obtain 3-benzyloxy-4-methoxyphenol, isovanillin which is also known 3-hydroxy-4-methoxybenzaldehyde is used as a starting material. Isovanillin is a commercially available material. If R is to be other than methyl then the appropriate 4-alkoxy compound is used as the starting material. The 4-alkoxy compound is made by alkylation of 3,4-dihydroxybenzaldehyde which is commercially available. Isovanillin is converted to 3-benzyloxy-4-methoxybenzaldehyde which is then converted to 3-benzyloxy-4-methoxyphenyl formate by the following reactions.

Performic acid is prepared by first heating a mixture of 30% by weight hydrogen peroxide and 97% by weight formic acid in a weight ratio of 1:5 to 60° C. and then cooling the mixture in an ice both. The mixture is then added dropwise over a three hour period to an ice-cold 1M solution of 3-benzyloxy-4-methoxybenzaldehyde in methylene chloride. After the addition is completed a saturated solution of sodium bisulfite is added dropwise until the mixture exhibits a negative starch-iodide test for peroxides. The reaction mixture is poured into an equal volume of water. The phases separate and the aqueous phase is extracted with two parts of methylene chloride per part of aqueous phase. The combined organic phases are washed with water, dried over magnesium sulfate and the solvent is evaporated. The 3-benzyloxy-4-methoxyphenyl formate is recrystallized from 95% by weight ethanol.

The 3-benzyloxy-4-methoxyphenyl formate is then converted to 3-benzyloxy-4-methoxyphenol by the following reaction. A mixture of 3-benzyloxy-4-methoxyphenyl formate, methanol and 1M sodium hydroxide in a weight ratio of 1:6:10 is heated under reflux conditions for one hour, the mixture is allowed to cool and an equal volume of water is added. The solution is washed with ether and acidified to pH 3 with concentrated hydrochloric acid. The resulting mixture is extracted with ether. The combined extracts are washed with water and dried over magnesium sulphate and the solvent is evaporated to yield a tan solid which is 3-benzyloxy-4-methoxyphenol.

The 3-benzyloxy-4-methoxyphenol is reacted with the $R_1$ chloroformate as follows. The phenol (1.0 equiv.) and triethylamine (1.1 equiv.) are first dissolved in methylene chloride. The $R_1$ chloroformate (1.1 equiv.) is added and the mixture is stirred for a number of hours. The solvent is then evaporated and the residue is dissolved in a 1:1 mixture of ether and ethyl acetate. This solution is washed with 1M hydrochloric acid, saturated sodium bicarbonate, and water, and dried over magnesium sulfate. The solvent is evaporated to yield the desired product.

The benzyl protecting group is then removed by catalytic hydrogenation. The above product is dissolved in absolute ethanol and 10 percent palladium on carbon is added. The mixture is placed on a Parr hydrogenator, which is then charged with hydrogen to a pressure of 50 lb./in.$^2$. Upon the cessation of hydrogen uptake (approximately 2-5 hours) the mixture is filtered through a celite pad and the solvent evaporated to yield the desired product.

Further details are described in McMurray et al. Journal Chemical Society, pages 1491-8 (1960) and Robinson et al. Journal Chemical Society, pages 3163-7 (1931).

The requisite chloroformate of the desired $R_1$ moiety is either commercially available, known in the art, or prepared from commercially available starting materials by known synthetic procedures.

Chloroformates, in general, can be prepared by the reaction of alcohols with phosgene. For a review of this method, as applied to the synthesis of chloroformates, see Matzner, Kurkjy, and Cotter, *Chemical Reviews*, 64, pages 645-687, (1964).

The alcohols used for preparation of the $R_1$ chloroformates ($R_1$OCOCl) are known compounds which are commercially available or preparable by standard organic preparative methods.

The synthetic procedures disclosed incorporate the benzyl group as a protecting agent for the phenolic hydroxy moiety during various synthetic reactions. Other groups may be employed in place of the benzyl group to achieve this protection. Examples of these groups include 2-methoxyethoxymethyl, methylthiomethyl, t-butyldimethylsilyl, t-butyl ethers, and the 2,2,2-trichloroethyl carbonate. Other protecting groups, as well as specific reaction conditions and references, can be found in "Protective Groups in Organic Synthesis" by Theodora W. Greene, John Wiley & Sons, NY, 1981, and in "Protective Groups in Organic Chemistry" by J. F. W. McOmie, Plenum Press, London, 1973.

The present new compounds form salts due to the presence of the phenolic hydroxy group. Thus, metal salts can be formed by reaction with alkali such as aqueous ammonia, alkali and alkaline earth metal compounds such as sodium, potassium and calcium oxides, hydroxides, carbonates and bicarbonate. The salts are of higher aqueous solubility than the parent compound and are useful for purification or isolation of the present products.

The following examples are presented to further illustrate this invention.

EXAMPLE 1

3-Hydroxy-4-methoxyphenyl 2-furfuryl carbonate

3-Benzyloxy-4-methoxyphenol (2.3 g.) and triethylamine (1.11 g.) are dissolved in 50 ml. of methylene chloride and the mixture was stirred at room temperature. To the mixture is added 2-furfuryl chloroformate (1.75 g.) and stirring continued for 2 hours. The reaction is quenched with water (1 ml.) and the solvent evaporated to leave a residue which is dissolved in ether and ethyl acetate followed by washing successively with 1M HCl, saturated sodium bicarbonate and water and drying over magnesium sulfate.

The solvent on evaporation yields the corresponding 3-benzyloxy compound which is dissolved in 250 ml. of absolute ethanol with 5% Pd/C, and placed in a Parr hydrogenator with $H_2$ gas at 50 lb./psi. After hydrogen uptake ceases the mixture is removed, filtered and evaporated to obtain the final product. The structure is confirmed using NMR methods.

The product is sweeter than sucrose.

EXAMPLE 2

A cherry flavored beverage is prepared by mixing 1.48 gms. of an unsweetened cherry flavored instant beverage base mix with 438 gms. of water, 0.13 gms. aspartame (APM) and 30 mgs. (0.007 weight percent) of 3-hydroxy-4-methoxyphenyl 2-furfuryl carbonate. The base contains a malic acid and monocalcium phosphate buffer.

EXAMPLE 3

A vanilla flavored pudding is prepared by mixing 474 gms. of milk, 21.7 gms. of an unsweetened pudding base mix containing 1.35 gms. of sodium acid pyrophosphate, 36.0 gms. sucrose (6.8 weight percent) and 27 mgs. (0.005 weight percent) of 3-hydroxy-4-methoxyphenyl 2-furfuryl carbonate.

EXAMPLE 4

Additional products are prepared using the procedure of Example 1, but substituting 2-furfuryl chloroformate by appropriate chloroformate esters to obtain the following products.

3-hydroxy-4-methoxyphenyl 3-tetrahydrofurfuryl carbonate
3-hydroxy-4-methoxyphenyl 2-thienylmethyl carbonate
3-hydroxy-4-methoxyphenyl 3-theinylmethyl carbonate
3-hydroxy-4-methoxyphenyl 3-furfuryl carbonate
3-hydroxy-4-methoxyphenyl 5-methyl-2-furfuryl carbonate
3-hydroxy-4-methoxyphenyl 5-methyl-2-thienylmethyl carbonate
3-hydroxy-4-methoxyphenyl 5-isopropyl-2-thienylmethyl carbonate
3-hydroxy-4-methoxyphenyl 2-tetrahydrothienylmethyl carbonate
3-hydroxy-4-methoxyphenyl N-acetyl-2-pyrrylmethyl carbonate
3-hydroxy-4-methoxyphenyl 5-acetyl-2-thienylmethyl carbonate
3-hydroxy-4-methoxyphenyl 5-methoxy-2-thienylmethyl carbonate
3-hydroxy-4-methoxyphenyl 3,5-dimethyl-2-thienylmethyl carbonate
3-hydroxy-4-methoxyphenyl 2-thiazolylmethyl carbonate
3-hydroxy-4-methoxyphenyl 5-thiazolylmethyl carbonate
3-hydroxy-4-methoxyphenyl 2-oxazolylmethyl carbonate
3-hydroxy-4-methoxyphenyl 2-imidazolylmethyl carbonate
3-hydroxy-4-methoxyphenyl 2-tetrahydrofurfuryl carbonate
3-hydroxy-4-methoxyphenyl 2-pyrrylmethyl carbonate

What is claimed is:

1. A compound of the formula:

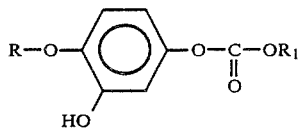

wherein:
R is methyl or ethyl;
$R_1$ is of the formula:

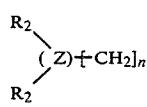

wherein Z is a five-membered heterocyclic ring in which the hetero atom is at least one of S, O, N and $NR_2$; wherein n is an integer from 0 to 1 when Z is a fully-saturated heterocyclic ring and, otherwise n=1;

each $R_2$ is selected from the group consisting of H, $CH_3$, $CH_2CH_3$, $CH_2CH_2CH_3$, $CH(CH_3)_2$, OH, $OCH_3$, $CH(OH)CH_3$, $OCH_2CH_3$, $OCH(CH_3)_2$, $CH_2OH$, $CH_2CH_2OH$, $CH_2CHOHCH_3$, $CH_2OCH_3$, CHO, $COCH_3$, $COCH_2CH_3$, $CH_2COCH_3$, and $COOCH_3$ with the proviso that $R_1$ contain no more than 12 carbon atoms; and salts thereof.

2. A compound of the formula:

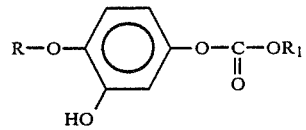

wherein:
R is selected rom the group consisting of methyl and ethyl;
$R_1$ is of the formula

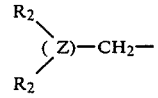

wherein Z is a five membered aromatic heterocyclic ring in which the hetero atom is at least one of S, O, N and $CR_2$; and
$R_2$ is selected from the group consisting of H, $CH_3$, $CH_2CH_3$, $CH_2CH_2CH_3$, $CH(CH_3)_2$, OH, $CCH_3$, $OCH_2CH_3$, $CH(OH)CH_3$, $OCH(CH_3)_2$, $CH_2OH$, $CH_2CHOHCH_3$, $CH_2OCH_3$, CHO, $COCH_3$, $COCH_2CH_3$, $CH_2COCH_3$, and $COOCH_3$ with the proviso that $R_1$ contain no more than 12 carbon atoms; and salts thereof.

3. A compound according to claim 2 with the proviso that $R_1$ contain no more than 10 carbon atoms.

4. A compound according to claim 2 with the proviso that $R_1$ contain no more than 8 carbon atoms.

5. A foodstuff containing a compound of the formula:

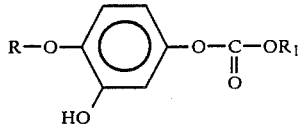

wherein:
R is methyl or ethyl;
$R_1$ is of the formula:

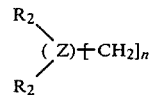

wherein Z is a five-membered heterocyclic ring in which the hetero is at least one of S, O, N and $NR_2$; wherein n is an integer from 0 to 1 when Z is a fully-saturated heterocyclic ring and, otherwise n=1;

each $R_2$ is selected from the group consisting of H, $CH_3$, $CH_2CH_3$, $CH_2CH_2CH_3$, $CH(CH_3)_2$, OH, $OCH_3$, $CH(OH)CH_3$, $OCH_2CH_3$, $OCH(CH_3)_2$, $CH_2OH$, $CH_2CH_2OH$, $CH_2CHOHCH_3$, $CH_2OCH_3$, CHO, $COCH_3$, $COCH_2CH_3$, $CH_2COCH_3$, and $COOCH_3$ with the proviso that $R_1$ contain no more than 12 carbon atoms; and salts thereof, said compound being present in an amount effective to perceive sweetness in said foostuff.

6. A foodstuff according to claim 5 wherein the foodstuff is a beverage.

7. A foodstuff according to claim 5 wherein the foodstuff is a gelatin dessert.

8. A foodstuff according to claim 5 wherein the foodstuff is a milk pudding.

9. The compound according to claim 2 which is 2-furfuryl 3-hydroxy-4-methoxyphenyl carbonate.

10. The compound according to claim 2 which is 2-thienylmethyl 3-hydroxy-4-methoxyphenyl carbonate.

* * * * *